United States Patent [19]
Jannard

[11] Patent Number: 4,674,851
[45] Date of Patent: Jun. 23, 1987

[54] REMOVABLE MULTI-COMPONENT SUNGLASSES

[76] Inventor: James H. Jannard, 30741 Fox Run La., San Juan Capistrano, Calif. 92675

[21] Appl. No.: 690,642
[22] Filed: Jan. 11, 1985
[51] Int. Cl.$^4$ .............................................. G02C 9/00
[52] U.S. Cl. ....................................... 351/47; 351/41
[58] Field of Search ............... 351/44, 47; 2/426, 429; 351/62, 103, 109, 158

[56] References Cited

U.S. PATENT DOCUMENTS

| D. 145,288 | 7/1946 | DiCicco . | |
|---|---|---|---|
| D. 163,869 | 7/1951 | Hinman . | |
| D. 176,316 | 12/1955 | Fleming . | |
| D. 187,394 | 3/1960 | Moeller . | |
| D. 199,150 | 9/1964 | Carmichael . | |
| D. 268,683 | 4/1983 | Tenny . | |
| D. 285,020 | 8/1986 | Schmidthaler . | |
| 2,444,498 | 7/1948 | Cochran . | |
| 2,472,731 | 6/1949 | Splaine . | |
| 2,582,345 | 1/1952 | Moeller . | |
| 3,233,249 | 2/1966 | Baratelli et al. | 351/44 |
| 3,233,250 | 2/1966 | Jonassen | 351/44 |
| 3,531,189 | 9/1970 | Petito . | |
| 3,689,136 | 9/1972 | Atamium . | |
| 4,515,448 | 5/1985 | Tackles | 351/41 |

FOREIGN PATENT DOCUMENTS

| 673815 | 4/1929 | France . |
|---|---|---|
| 790755 | 5/1935 | France . |
| 2472764 | 12/1979 | France . |

Primary Examiner—Rodney B. Bovernick
Assistant Examiner—P. M. Dzierzynski
Attorney, Agent, or Firm—William W. Haefliger

[57] ABSTRACT

Sunglasses have a unitary transparent pane extending in a cylindrical plane. The sunglasses frame and nose-piece construction permits their ease of removal and replacement, as well as pane replacement.

7 Claims, 12 Drawing Figures

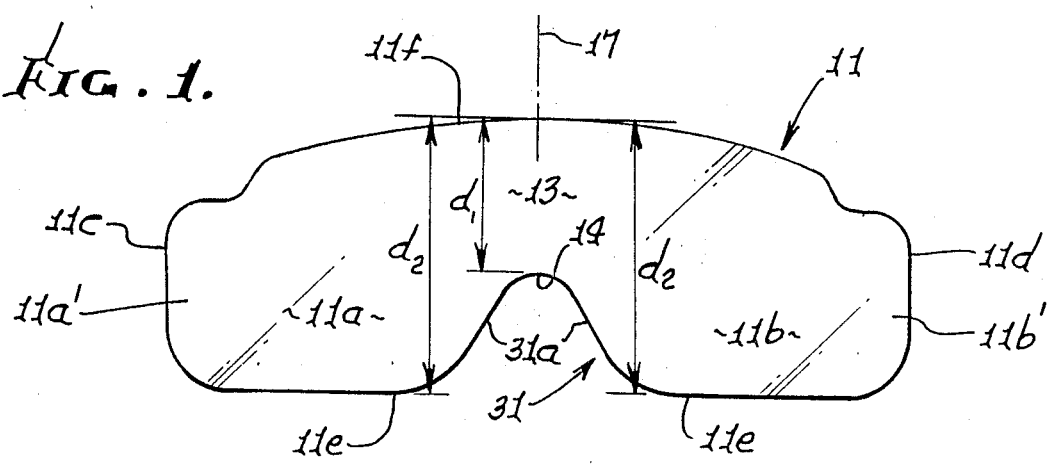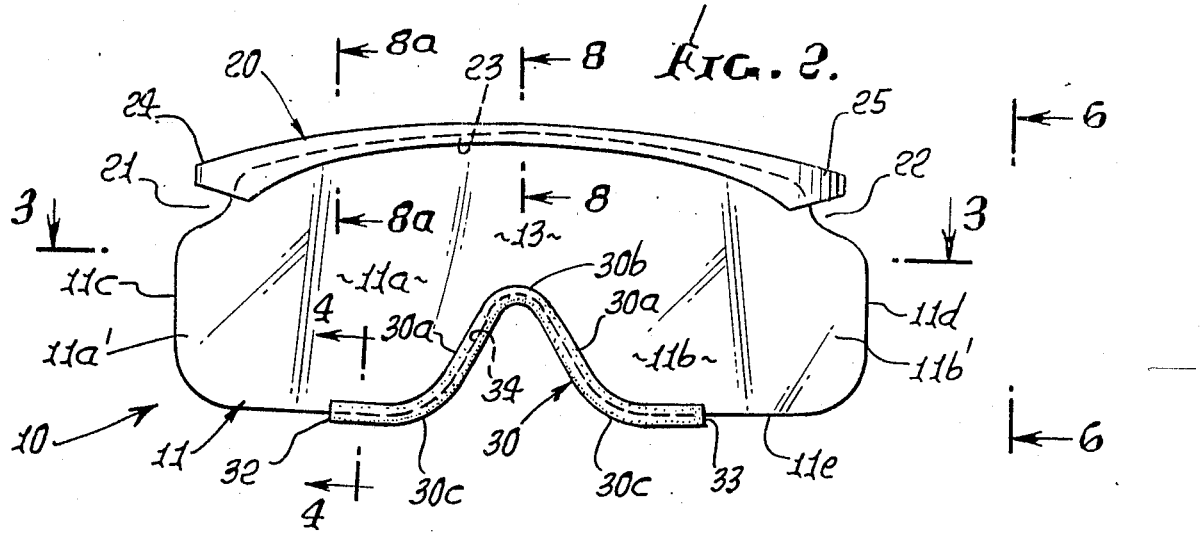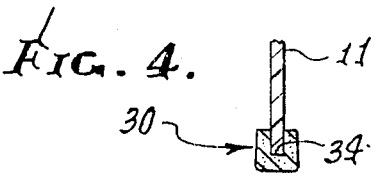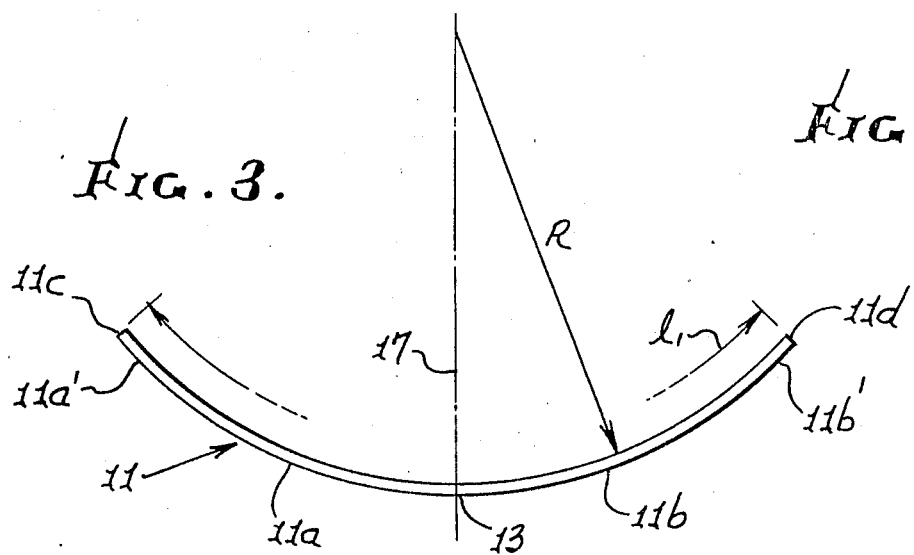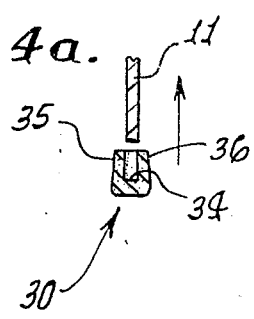

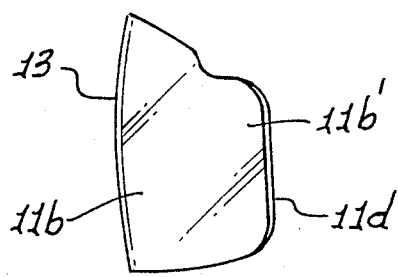
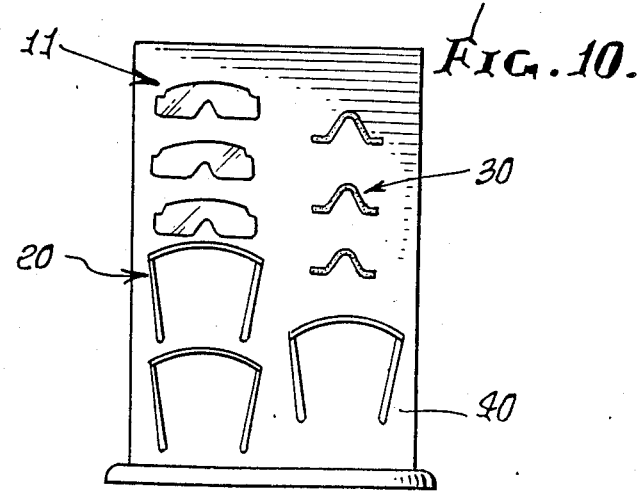
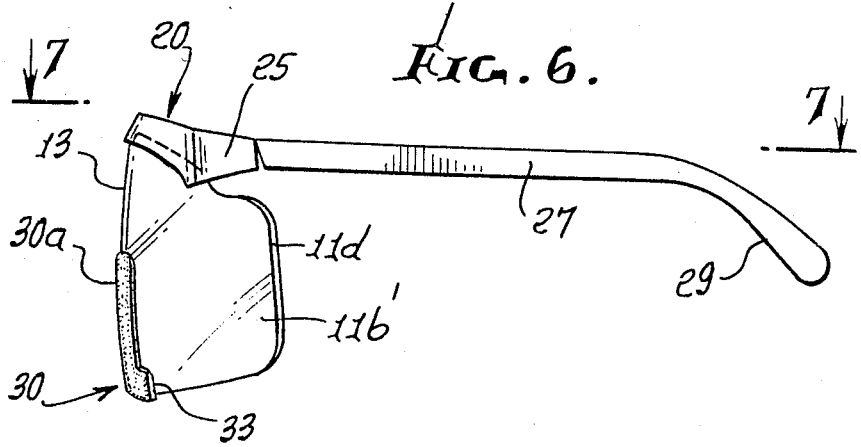
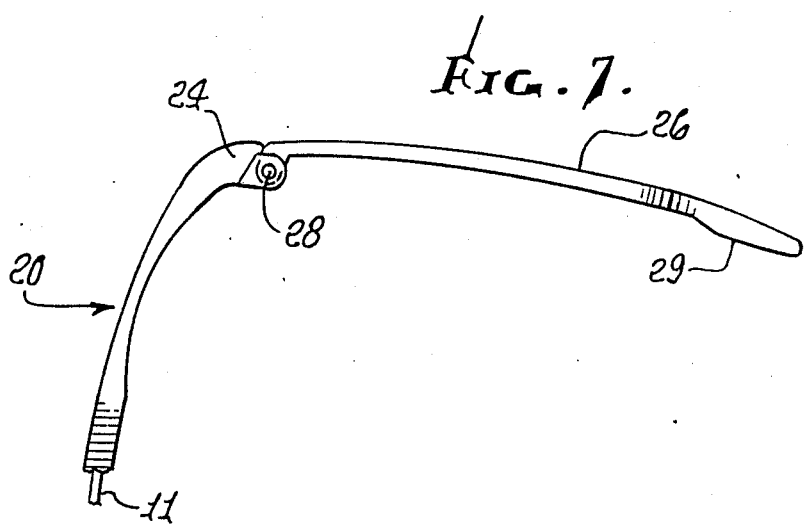
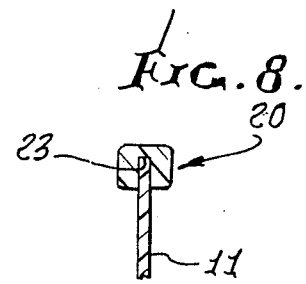
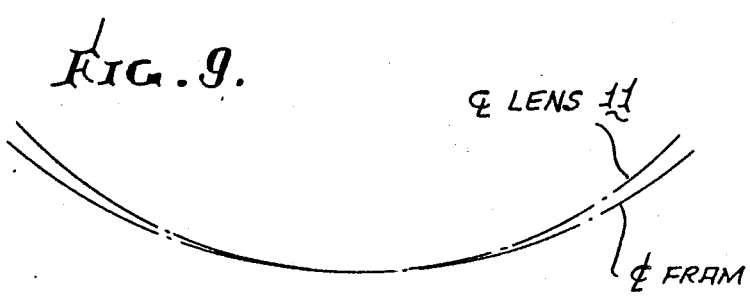
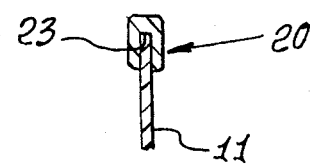

REMOVABLE MULTI-COMPONENT SUNGLASSES

BACKGROUND OF THE INVENTION

This invention relates generally to eyewear, and more particularly to construction of sunglasses.

There is a need for sunglasses which more completely intercept sunlight at the top, bottom and sides of the glasses; also there is need for sunglasses which permit ease of pane or lens removal and replacement, and also replacement or substitution of different nose pieces and frames, to better fit the wearer. There is also need for simplicity of frame, nose piece and lens assembly construction, together with means to reduce air turbulence and moisture on the lens, near the eyes of the wearer.

SUMMARY OF THE INVENTION

It is a major object of the invention to provide improved sunglasses which meet the above needs, and which also incorporate other unusual advantages in construction, modes of adjustment, and results, as will appear. Basically, the improved eyeglasses comprise a unitary transparent lens or pane located to extend in the paths of the wearer's fields of vision, frontwardly and sidewardly; and the lens extends in a plane which is cylindrical, wrapping around the sides of the head to intercept peripheral vision. The result is better interception of sunlight, top to bottom and side-to-side, the lens matching closely the wearer's facial contour. No distortion is introduced because of absence of local suddenly increased curvature or breaks in shape.

As will be seen, the protective eyeglasses or sunglasses basically comprise:

(a) a unitary transparent pane located to extend in a curved plane in the path of the wearer's field of vision, both frontally and sidewardly, that curved plane being substantially cylindrical, the pane having an upwardly humped lower edge bounding a space to receive the wearer's nose, (b) a top frame extending along and bounding upper edge extent of the pane, and arms attached to the top frame at opposite ends thereof and adapted to extend rearwardly to the wearer's ears, (c) and a nose piece bounding the unitary pane upwardly humped lower edge, and having laterally spaced terminals located along the bottom edge of said pane, (d) at least one of said top frame and nose piece having removable attachment to said pane.

As will be seen, both the top frame and nose piece typically have removable attachments to the unitary pane, such attachments being independent to permit selective removal and replacement of the nose piece and top frame, as well as the pane iteself; in this regard, the wearer can thereby easily assemble these components from a group of same, of different sizes, to best fit his facial and head contours. Preferably, the curved pane is cylindrical in the as-molded condition, and it consists of synthetic resin.

Another object of the invention is to provide a replaceable nose piece that consists of a relatively soft elastomeric material having a coefficient of sliding friction that increases when said material is wetted, such material typically being hydrophilic.

It is a further object to provide sunglasses having a unitary plastic pane free of frame structure along frame edges extending downwardly from locations proximate the attachments of the arms to the top frame, and then inwardly toward the nose piece terminals, whereby the top frame is removable relatively upwardly off the unitary pane, and the nose piece is removable relatively downwardly from the unitary pane.

These and other objects and advantages of the invention, as well as the details of an illustrative embodiment, will be more fully understood from the following specification and drawings, in which:

DRAWING DESCRIPTION

FIG. 1 is a front view of a unitary pane, in flattened condition;

FIG. 2 is a frontal view of sunglasses incorporating the invention;

FIG. 3 is a section through the cylindrically normal pane of FIG. 2, on lines 3—3 of FIG. 2;

FIG. 4 is an enlarged section on lines 4—4 of FIG. 2; and FIG. 4a is like FIG. 4, prior to assembly of the nose piece to the pane;

FIG. 5 is a side view of the curved pane, in as-molded condition;

FIG. 6 is a side view of the assembled sunglasses, on lines 6—6 of FIG. 2;

FIG. 7 is a top plan view showing frame arm hinge structure;

FIG. 8 is an enlarged section on lines 8—8 of FIG. 2; and FIG. 8a is a section on lines 8a—8a of FIG. 2; and FIG. 9 is a diagram to show mismatch between interfits of the pane and top frame; and FIG. 10 is a display.

DETAILED DESCRIPTION

The protective eyeglasses, as for example sunglasses shown at 10 in FIG. 2, include transparent panes or lenses 11a and 11b located to extend in the direct path of the wearer's left and right eye fields of vision. Those panes merge as at bridge 13 directly above the wearer's nose, a generally triangular nose opening being formed at 14. Thus, a unitary or single pane or lens 11 is provided, and may be easily replaced, as for example by panes of lesser or greater darkness, size, or different coloring, etc., as desired by the wearer.

It is a feature of the invention that the unitary pane extends in a plane which is cylindrical in as-molded condition i.e. as indicated by FIG. 3. "As molded condition" means that when the pane is molded, it has curvature as specified. FIG. 3 shows the cylindrical curvature of the single pane, and between opposite end wings 11a' and 11b'. FIG. 1 shows the pane in flattened condition, i.e. pressed into the flat plane of the paper. The panes 11a and 11b and bridge 13 are formed to have cylindrical conformation such that their curvatures conform very well to the natural curvature of the wearer's face, i.e. his cheek bones and forehead as well as side face configuration. Note that panes 11a and 11b and wings 11a' and 11b' wrap backwardly or rearwardly to extend inthe paths of the wearer's sideward fields of vision, without such abruptly changing curvature as would distort the light passing through the side wrapping portions of the panes. The curved planes of panes 11a and 11b are symmetrically located at opposite sides of a plane 17 bisecting the bridge 13, and contained by the axis of the cylinder defined by the panes. For best result, the radius R of curvature of the panes is in the range 3.25 to 5.00 inches, and optimally within the range 3.50 and 4.00 inches.

Also, the pane 11 has a vertical dimension $d_1$ immediately above the nose bridge, $d_1$ being between $\frac{3}{4}$ inch and $1\frac{1}{2}$ inch; the pane has generally rearwardly extending lateral terminals 11c and 11d and a length dimension $l_1$ between said terminals, $l_1$ between $5\frac{1}{2}$ and 7 inches, that length dimension measured along the cylindrical curvature of the pane; and the pane has two lowermost terminals 11e, and width dimensions $d_2$ between 2 and $2\frac{3}{4}$ inches, as measured between those lowermost terminals 11e and the pane uppermost top edge 11f.

Also provided is a top frame 20 extending along and bounding upper edge extent of the lens or pane 11, as between the notched areas 21 and 22 formed immediately above the wings 11a' and 11b'. The frame may advantageously consist of relatively rigid, molded plastic material, which may be transparent. The top frame is shown as having removable attachment to the top edge extent of the lens or pane, and for this purpose a slot 23 is formed upwardly therein from the bottom of the frame 20, with curvature generally matching that of the lens, to tightly, yet removably receive the lens upper edge extent. For this purpose, the curvature of the slot 23 may slightly different than the cylindrical, as-molded curvature of the lens, to provide a mismatch, to grip the pane. See FIG. 9. Note that the lens upper edge 11f is shown to have slight upward convexity, in FIG. 1, as well as cylindrical curvature, as in FIG. 3.

The top frame has enlarged end terminals at 24 and 25, that extend in notched areas 21 and 22, and have hinged attachment to two arms 26 and 27 adapted to extend rearwardly to the wearer's ears. See for example the hinge pins 28 interconnecting the arms and end terminals 24 and 25. Arms hook at 29 over the wearer's ears, and the arms may also consist of molded plastic material.

A nose piece 30 bounds the pane upwardly humped lower edge 31, and has terminals 32 and 33 which are laterally spaced apart to be located along the lowermost bottom edges of the pane, as at 11e. The nose piece has upwardly extending sections 30a which taper toward one another, in matching relation to pane edges 31a. An upwardly convex section 30b interconnects the sections 30a; and downwardly convex sections 30c of the nose piece extend between the sections 30a and the terminals 32 and 33. The nose piece has a slot 34 formed therein to extend along the wave-shaped length of the nose piece for removable interfit with the pane upwardly humped lower edge, as seen in FIGS. 2 and 4. FIG. 4a shows the nose piece as channel shaped in cross section, with flanges 35 and 36 that taper toward one another, to be spread apart upon reception of the pane, as seen in FIG. 4, providing a removable grip or retention of these elements. The nose piece typically consists of a relatively soft elastomeric material having a coefficient of sliding friction that increases when the material is wetted. Such a material is hydrophilic, and tends to retain the nose piece in position on the wearer's upper nose area as the wearer perspires, or encounters moisture as during skiing. Also, the material is soft, for comfort. One such material is KROTON G, a product of Shell Oil Company.

The nose piece may be removed, relatively downwardly, and replaced with a selected substitute, having different size, shape or color, to meet the needs of the wearer; also the top frame may be easily removed upwardly from the pane, and replaced with a different size or color frame; or, the pane itself may be replaced with a substitute having different sun blocking shading or composition, color, etc. Thus, the wearer or user may assemble his sunglasses from a large number of different components, as provided on a rack or other display, to result in an assembled sunglasses truly best fitted and best suited, component wise, in every respect to the requirements of the wearer. One such rack is shown at 40 in FIG. 10, with a number of different panes 11, frames 20 and nose pieces 30, having different size, color, etc., characteristics, but interfittable as described above, to provide a custom sunglasses, easily selected, compared, and assembled, by the wearer or dealer.

The notches or notched areas 21 and 22 that extend downwardly proximate the attachments of the hinged connections of the arms to the top frame also open sidewardly. It is found such upper notches draw discharge moisture collecting on rearward surfaces of pane, and below the top frame (which projects rearwardly from the top of the pane). Such discharge is believed due to an aspirating effect of air directed laterally toward the notches at the front of the pane, during forward movement of the wearer (as for example a skier). Also, air turbulence at the rearside of the pane is reduced due to presence of the notches. Accordingly, the wearer's eyes are further protected from air turbulence and moisture, as during skiing, wind surfing, etc.

I claim:

1. In protective eyeglasses, a combination of the following:
    (a) a unitary transparent pane located to extend in a curved plane in the path of a wearer's field of vision, both frontally and sidewardly, said curved plane being everywhere substantially cylindrical, and having the same radius of curvature, the pane have an upwardly humped lower edge bounding a space to receive the wearer's nose,
    (b) a top frame extending along and bounding elongated upper edge extent of the pane, and arms attached to the top frame at opposite ends thereof and adapted to extend rearwardly to the wearer's ears,
    (c) a nose piece having a slot therein and extending therealong to removably receive and closely fit the pane upwardly humped lower edge,
    (d) and the top frame having a slot therein and extending therealong to removably vertically receive and closely fit the pane upper edge,
    (e) the top frame and nose piece independently attached to the pane via the slots in the top frame and nose piece to permit selective removal and replacement of the top frame and nose piece,
    (f) the pane being notched downwardly proximate the attachments of the arms to the top frame, the notches opening sidewardly above opposite end extents of the pane to draw and discharge moisture collecting on rearward surfaces of the pane during forward movement of the wearer, the top frame overhanging said notches,
    (g) the pane being substantially cylindrical in the as-molded condition of said pane, the pane having an associated radius of curvature between 3.25 and 5.00 inches, the pane having a vertical dimension $d_1$ immediately above said nose bridge, $d_1$ being between $\frac{3}{4}$ inch and $1\frac{1}{2}$ inch, the pane also having generally rearwardly extending lateral terminals below said notches, the pane having a length dimension $l_1$ between said terminals between $5\frac{1}{2}$ and 7 inches, said length dimension measured along the curvature of the pane.

2. The combination of claim 1 wherein said pane consists of synthetic resin.

3. The combination of claim 2 wherein said radius is between 3.50 and 4.00 inches.

4. The combination of claim 3 wherein said nose piece consists of a relatively soft elastomeric material having a coefficient of sliding friction that increases when said material is wetted.

5. The combination of claim 4 wherein said material is hydrophilic.

6. The combination of claim 1 wherein the pane has two lowermost terminals, the pane having width dimensions between 2 and 2¾ inches, as measured between said lowermost terminals and lateral extensions of a tangent to the pane top edge over said upwardly humped lower edge.

7. The combination of claim 1 wherein said eyeglasses comprise sunglasses, the pane being darkened.

* * * * *